US00PP26296P3

(12) United States Plant Patent
Klemm et al.

(10) Patent No.: US PP26,296 P3
(45) Date of Patent: Jan. 5, 2016

(54) ***GENTIANA* PLANT NAMED 'KLEGH12013'**

(50) Latin Name: ***Gentiana* sp.**
Varietal Denomination: KLEGH12013

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 195 days.

(21) Appl. No.: 13/998,341

(22) Filed: Oct. 23, 2013

(65) Prior Publication Data

US 2015/0113693 P1 Apr. 23, 2015

(51) Int. Cl.
*A01H 5/02* (2006.01)

(52) U.S. Cl.
USPC ..... Plt./433

(58) Field of Classification Search
USPC ..... Plt./433
See application file for complete search history.

*Primary Examiner* — June Hwu
(74) *Attorney, Agent, or Firm* — James M. Weatherly; Bethany R. Roahrig; Cochran Freund & Young, LLC

(57) ABSTRACT

A new *Gentiana* plant particularly distinguished by having a compact plant habit with short internodes, and medium sized, light blue flowers, is disclosed.

1 Drawing Sheet

Genus and species: *Gentiana* sp.
Variety denomination: 'KLEGH12013'.

BACKGROUND OF THE NEW PLANT

The present invention comprises a new and distinct variety of gentian, botanically known as *Gentiana* sp. and hereinafter referred to by the variety name 'KLEGH12013'. 'KLEGH12013' originated from a cross between the proprietary female *Gentiana* variety 'GH 2005-0006' (unpatented) and an unknown male *Gentiana* sp. variety.

In August 2006, two *Gentiana* parental lines, were crossed in Stuttgart, Germany and seeds were obtained. The seeds were sown and plants were grown for evaluation. A plant line was selected in July 2008, and subsequently named 'KLEGH12013'. In August 2008, 'KLEGH12013' was first vegetatively propagated by tissue culture and vegetative cuttings. 'KLEGH12013' was found to reproduce true to type in successive generations of asexual propagation via shoot apex and stem cuttings in Stuttgart, Germany.

CROSS REFERENCE TO RELATED APPLICATIONS

Plant Breeder's Rights for 'KLEGH12013' were applied for in Switzerland on Jun. 6, 2013, Application No. 13-2873 and in Europe on Jun. 25, 2013 as Application No. 2013/1711. 'KLEGH12013' has not been made publicly available or sold more than one year prior to the filing date of this application.

SUMMARY

The following are the most outstanding and distinguishing characteristics of this new variety when grown under normal horticultural practices in Stuttgart, Germany.

1. Compact plant habit with short internodes; and
2. Medium sized, light blue flowers.

DESCRIPTION OF THE PHOTOGRAPH

This new *Gentiana* plant is illustrated by the accompanying photograph which shows overall habit of the plant. The photograph is of a plant approximately five-months-old grown in Stuttgart, Germany in September 2010.

The colors shown are as true as can be reasonably obtained by conventional photographic procedures.

DESCRIPTION OF THE NEW VARIETY

The following detailed descriptions set forth the distinctive characteristics of 'KLEGH12013'. The data which define these characteristics were collected from asexual reproductions carried out in Stuttgart, Germany. Data was collected on 20-week-old plants in a greenhouse in Stuttgart, Germany in July 2013. Color references are to The R.H.S. Colour Chart of The Royal Horticultural Society of London (R.H.S.), 5$^{th}$ edition (2007).

Classification:
- *Family*.—Gentianaceae.
- *Common name*.—Gentian.

Parentage:
- *Female parent*.—*Gentiana* proprietary line 'GH 2005-0006'.
- *Male parent*.—Unknown.

Propagation:
- *Type*.—Shoot apex and stem cuttings.
- *Time to initiate roots*.—Two weeks.
- *Time to produce a rooted young plant*.—Five weeks.
- *Root description*.—Fine.
- *Rooting habit*.—Moderately branching.

Plant description:
- *Plant and growth habit*.—Compact, round-shaped, freely-branching.
- *Plant height*.—8.0 cm including flowers.
- *Plant diameter or spread*.—15.0 cm.

Flowering stem description:
- *Diameter*.—0.1 cm.
- *Internode length*.—Approximately 0.5 cm.
- *Strength*.—Medium.
- *Texture*.—Smooth.
- *Color*.—RHS 144D.

Foliage description:

*Arrangement*.—Opposite, sessile.
*Length*.—1.5 cm to 2.0 cm.
*Width*.—0.8 cm to 1.0 cm.
*Shape*.—Ovate.
*Apex*.—Acute.
*Base*.—Obtuse.
*Margin*.—Entire.
*Texture*.—Upper and lower surfaces: Smooth.
*Venation pattern*.—Parallel.
*Venation color*.—RHS 144D.
*Foliage color*.—Developing leaves: Upper surface: RHS 143B. Lower surface: RHS 143C. Fully expanded leaves: Upper surface: Between RHS 141A and RHS 139A. Lower surface: RHS 141C.

Flower description:

*Flower arrangement, shape and habit*.—Single, sessile, campanulate flowers, 1 to 2 per stem.
*Natural flowering season*.—July and August.
*Flower longevity as a single flower*.—Single flower longevity on the plant about 10 days.
*Fragrance*.—Absent.
*Petaloids*.—Absent.
*Opening*.—One flower at a time.

Flower clusters:

*Quantity of flowers per cluster*.—1 to 2.
*Height* (*single flower*).—2.5 cm to 3.0 cm.
*Diameter* (*single flower, measured on top of open flower*).—Approximately 2.5 cm.

Flower buds:

*Length*.—2.0 cm.
*Diameter*.—0.3 cm.
*Shape*.—Oblong.
*Color*.—RHS 144D.

Petals:

*Arrangement*.—5 fused petals.
*Length*.—2.5 cm to 3.0 cm.
*Width*.—Approximately 0.8 cm.
*Shape*.—Oblong.
*Apex*.—Acute.
*Base*.—Fused.
*Margin*.—Slightly serrate.
*Texture*.—Upper and lower surfaces: Smooth.
*Color*.—When opening: Upper and lower surfaces: RHS 95C. Fully opened: Upper surface: Blue between RHS 95C and RHS 94A; spots and streaks only on the upper surface, both RHS 198D; base: RHS 139D. Lower surface: Blue between RHS 95C and RHS 94A and stripes of RHS N77C; base: the base of the blue part as well as of the grey purple stripes has RHS 139D.
*Corolla tube shape*.—Funnel form.
*Corolla lobe curvature*.—Incurved asymmetrically.

Sepals:

*Arrangement*.—5 in a single whorl.
*Length*.—1.0 cm to 1.2 cm.
*Width*.—0.3 cm to 0.4 cm.
*Shape*.—Lanceolate.
*Apex*.—Acute.
*Base*.—Fused.
*Margin*.—Entire.
*Texture*.—Upper and lower surfaces: Smooth.
*Color*.—Developing: Upper surface: Between RHS 141A and RHS 139A. Lower surface: RHS 141C. Fully developed: Upper surface: Between RHS 141A and RHS 139A. Lower surface: RHS 141C.

Reproductive organs:

*Stamens*.—Quantity per flower: 5. Anther shape: Oblong. Anther length: 0.3 cm. Anther color: RHS 12C.
*Pollen amount*.—Sparse to moderate.
*Pollen color*.—RHS 12C.
*Pistils*.—Quantity per flower: 1. Pistil length: 2.0 cm. Stigma shape: Divided in 2 parts. Stigma color: RHS 1D. Style length: 1.3 cm. Style color: RHS 144D. Ovary color: RHS 142C.

Seed/fruit production: Not observed.
Disease/pest resistance: Not observed.
Temperature tolerance: Tolerates temperatures down to −20° C. (if soil is dry) and up to 32° C.

COMPARISON WITH FEMALE PARENTAL LINE AND KNOWN VARIETY

'KLEGH12013' is distinguished from its female parent as described in Table 1:

TABLE 1

| Trait | Variety 'KLEGH12013' | Female parent 'GH 2005-0006' |
|---|---|---|
| Vigor | Compact | Vigorous |
| Leaf shape | Ovate | Lanceolate |

'KLEGH12013' is most similar to the commercial *Gentiana* plant named 'Shusui Blue' (Patent status unknown). Differences between the two varieties are described in Table 2:

TABLE 2

| Comparison with Similar Variety | | |
|---|---|---|
| Trait | Variety 'KLEGH12013' | Commercial line 'Shusui Blue' |
| Habit | Compact, short internodes | More vigorous with longer internodes than 'KLEGH12013' |
| Flowers | Medium sized, light blue | Larger sized, with a darker blue than 'KLEGH12013' |

It is claimed:

1. A new and distinct variety of *Gentiana* plant named 'KLEGH12013' as illustrated and described herein.

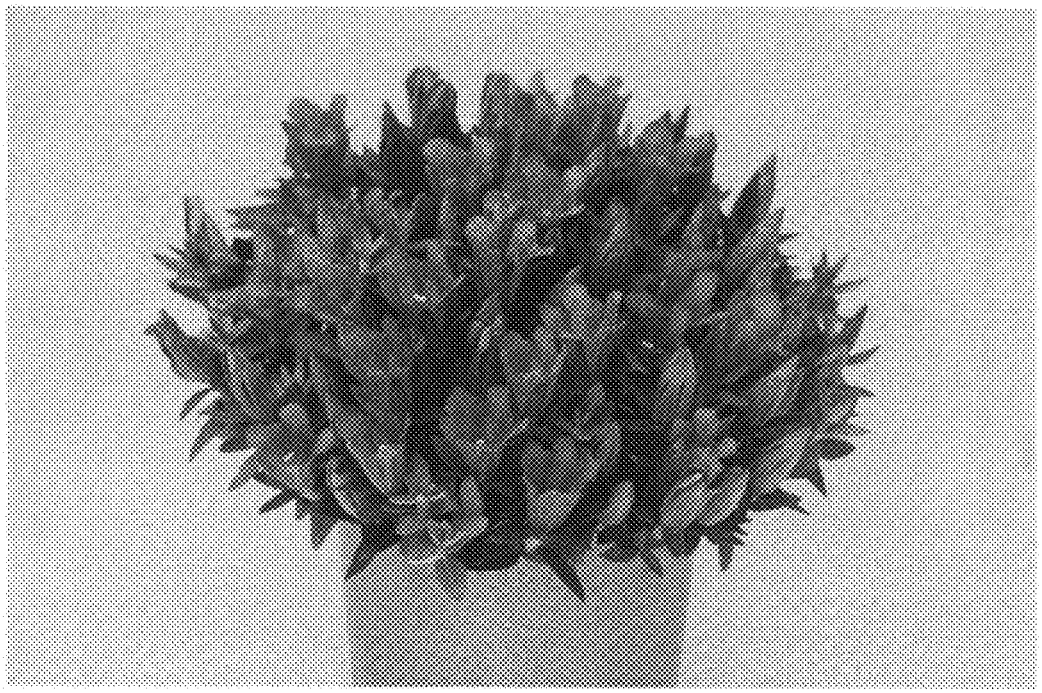

* * * * *